United States Patent
Petrick et al.

(10) Patent No.: US 8,941,070 B2
(45) Date of Patent: Jan. 27, 2015

(54) PORTABLE DIGITAL IMAGE DETECTOR POSITIONING APPARATUS

(75) Inventors: Scott W. Petrick, Sussex, WI (US); Alan D. Blomeyer, Milwaukee, WI (US); James Z. Liu, Glenview, IL (US); Emad Abu Tabanjeh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1468 days.

(21) Appl. No.: 12/274,220

(22) Filed: Nov. 19, 2008

(65) Prior Publication Data

US 2010/0123083 A1    May 20, 2010

(51) Int. Cl.
*A61B 6/12* (2006.01)
*G01T 1/161* (2006.01)
*A61B 6/00* (2006.01)

(52) U.S. Cl.
CPC ............. *A61B 6/4411* (2013.01); *A61B 6/4233* (2013.01); *A61B 6/4464* (2013.01); *A61B 6/547* (2013.01); *A61B 6/587* (2013.01)
USPC .............. 250/361 R; 250/370.09; 250/370.11

(58) Field of Classification Search
USPC ............ 250/361 R, 370.09, 370.11; 378/117, 378/189, 205
See application file for complete search history.

(56) References Cited

U.S. PATENT DOCUMENTS

| | | | |
|---|---|---|---|
| 6,979,826 B2 | 12/2005 | Ikhlef | |
| 7,211,803 B1 | 5/2007 | Dhurjaty et al. | |
| 7,343,001 B2 | 3/2008 | Abu Tabanjeh | |
| 7,414,565 B2 | 8/2008 | Liu et al. | |
| 7,429,737 B2 | 9/2008 | Wojcik et al. | |
| 7,627,084 B2 | 12/2009 | Jabri et al. | |
| 7,633,077 B2 | 12/2009 | Kito | |
| 7,772,560 B2 * | 8/2010 | Ohta et al. | 250/370.09 |
| 2002/0085670 A1 * | 7/2002 | Vafi et al. | 378/98.8 |
| 2003/0194056 A1 * | 10/2003 | Spahn | 378/205 |
| 2005/0031087 A1 * | 2/2005 | Maschke | 378/196 |
| 2005/0063512 A1 * | 3/2005 | Maschke | 378/91 |
| 2006/0169907 A1 * | 8/2006 | Shinden | 250/370.09 |
| 2006/0215892 A1 * | 9/2006 | Ohara | 382/128 |
| 2007/0140424 A1 * | 6/2007 | Serceki | 378/62 |
| 2008/0240358 A1 * | 10/2008 | Utschig et al. | 378/107 |
| 2010/0230606 A1 * | 9/2010 | Liu et al. | 250/370.04 |
| 2010/0246757 A1 * | 9/2010 | Liu et al. | 378/19 |

FOREIGN PATENT DOCUMENTS

JP    2002336225 A    11/2002

* cited by examiner

*Primary Examiner* — Casey Bryant
(74) *Attorney, Agent, or Firm* — Fletcher Yoder, P.C.

(57) ABSTRACT

An imaging system is provided. In one embodiment, an imaging system includes a radiation source and a digital detector. The imaging system may also include first and second structures, each configured to receive the digital detector. Further, the imaging system may include system control circuitry configured to control exposure of the digital detector by the radiation source and to acquire image data from the digital detector. Additionally, the digital detector may be configured to communicate its location to the system control circuitry based on receipt of the digital detector by the first or second receiving structures. Additional systems, methods, and devices are also disclosed.

18 Claims, 9 Drawing Sheets

FIG. 9

PORTABLE DIGITAL IMAGE DETECTOR POSITIONING APPARATUS

BACKGROUND

The present invention relates to digital imaging systems, and particularly to a technique for determining the position of a portable, digital image detector in such systems.

A number of radiological imaging systems of various designs are known and are presently in use. Such systems generally are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Increasingly, such X-ray systems use digital circuitry, such as solid-state detectors, for detecting the X-rays, which are attenuated, scattered or absorbed by the intervening structures of the subject. Additionally, these digital detectors may be portable, and more than one digital detector may be present in a general area for imaging, such as within a room in a medical facility for taking X-ray images of a patient. If the room or other area has multiple digital detectors, however, it is possible that a technician may place one of the detectors in position to receive X-rays from a radiation source of the imaging system, while the imaging system may instead interact with a different digital detector that is not in position to receive X-rays passing through the patient or other object of interest. In such an instance, additional exposures may be needed to receive the desired image data from the appropriately positioned detector, and such additional exposures may not provide any additional diagnostic benefit to a patient.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Some embodiments of the present invention may generally relate to techniques for facilitating determination of the position of one or more digital detectors of an imaging system by a system controller. In one embodiment, a digital detector configured for use with an imaging system includes first and second sensors configured to be alternatively activated by respective first and second actuators at different locations in the imaging system. A system controller of the imaging system may generally determine whether a detector is positioned at one of the actuator locations based on activation of the corresponding sensor in the detector. In some embodiments, the detector may be armed for use in other positions apart from the actuators, and the system controller may synchronize an exposure with the armed detector.

Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
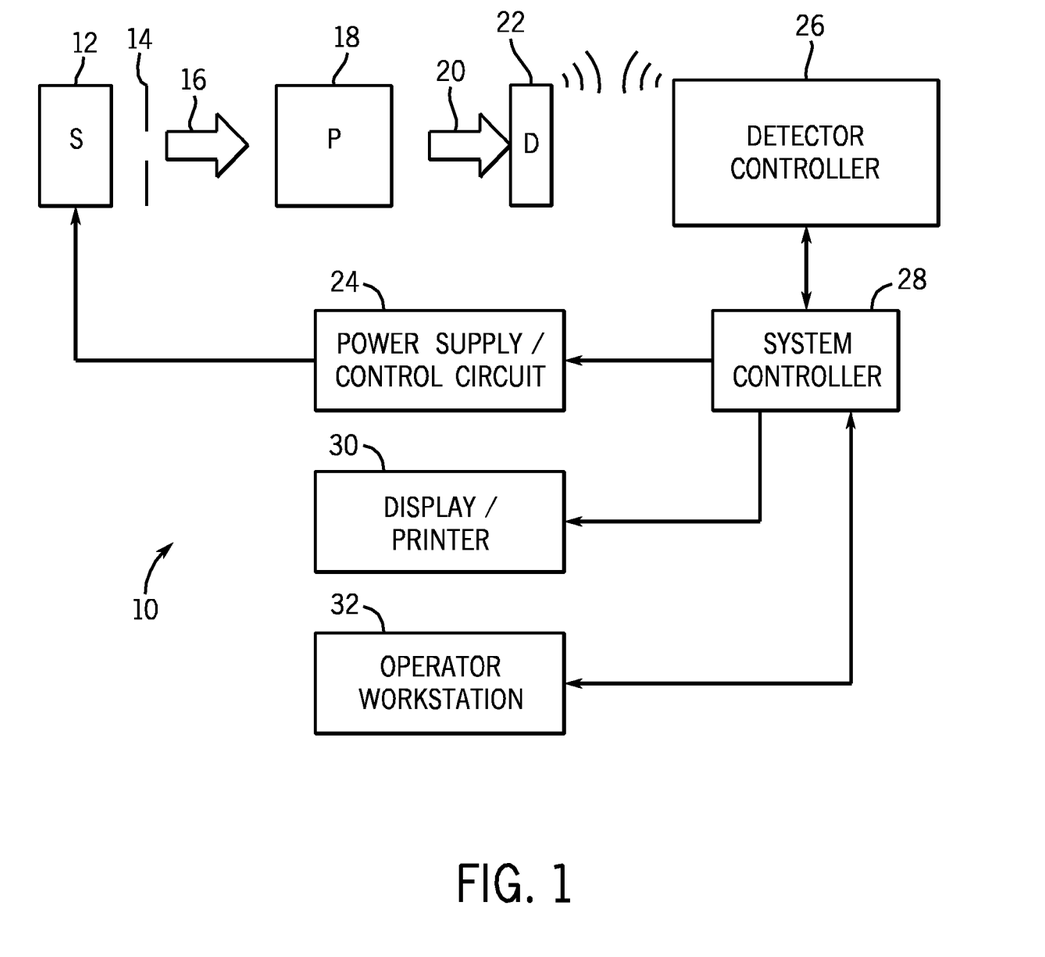
FIG. 1 is a diagrammatical overview of a digital X-ray imaging system of one embodiment in which the present technique may be utilized.

Turning now to the drawings, FIG. 1 illustrates diagrammatically an imaging system 10 for acquiring and processing discrete pixel image data. In the illustrated embodiment, the imaging system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. The collimator 14 permits a stream of radiation 16 to pass into a region in which an object or subject, such as a patient 18, is positioned. A portion of the radiation 20 passes through or around the subject and impacts a digital X-ray detector, represented generally at reference numeral 22. As will be appreciated by those skilled in the art, the detector 22 may convert the X-ray photons received on its surface to lower energy photons, and subsequently to electric signals, which are acquired and processed to reconstruct an image of the features within the subject.

The radiation source 12 is controlled by a power supply/control circuit 24 which supplies both power and control signals for examination sequences. Moreover, the detector 22 is communicatively coupled to a detector controller 26 which commands acquisition of the signals generated in the detector 22. In the presently illustrated embodiment, the detector 22 may communicate with the detector controller 26 via any suitable wireless communication standard, although the use of detectors 22 that communicate with the detector controller 26 through a cable or some other mechanical connection are also envisaged. The detector controller 26 may also execute various signal processing and filtration functions, such as for initial adjustment of dynamic ranges, interleaving of digital image data, and so forth.

Both the power supply/control circuit 24 and the detector controller 26 are responsive to signals from a system controller 28. In general, the system controller 28 commands operation of the imaging system to execute examination protocols and to process acquired image data. In the present context, the system controller 28 also includes signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface circuits; and so forth.

In the embodiment illustrated in FIG. 1, the system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
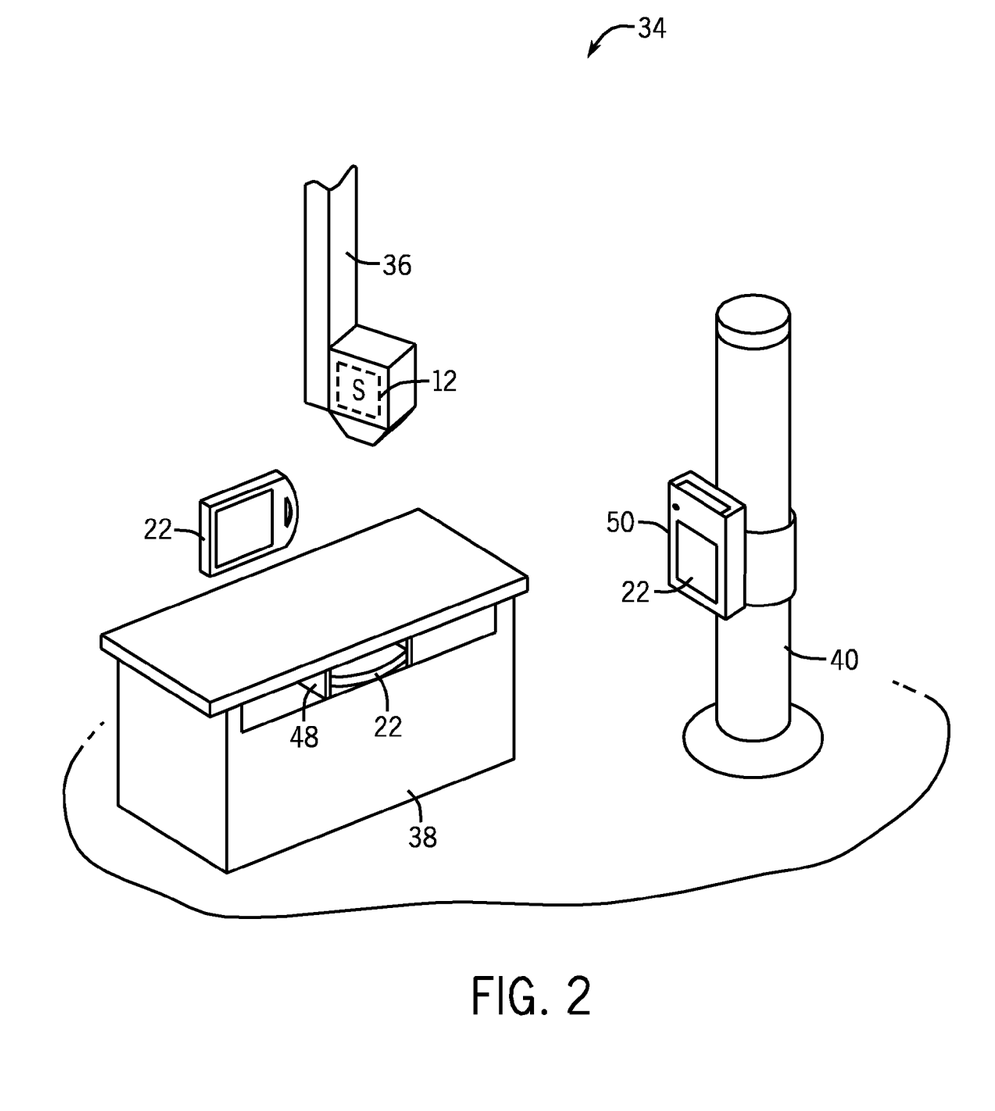
FIG. 2 is a perspective view of the digital X-ray imaging system of FIG. 1 in accordance with one embodiment.

By way of further example, a perspective view of an imaging system 34 is provided in FIG. 2 in accordance with one embodiment. In the presently illustrated embodiment, the imaging system 34 is an X-ray imaging system including an overhead tube support 36 for positioning a radiation source 12, such as an X-ray tube. Further, in addition to the radiation source 12, the imaging system 34 of the present embodiment may include each of the components described above with respect to FIG. 1, including the system controller 28.

Moreover, the imaging system 34 may also include a patient table 38 and a wall stand 40 to facilitate image acquisition. Particularly, the table 38 and the wall stand 40 may be configured to receive one or more digital detectors 22. In the presently illustrated embodiment, the table 38 includes a structure 48, such as a receptacle or some other support apparatus, configured to receive one of the digital detectors 22. Similarly, the wall stand 40 may include a receiving structure 50 also adapted to receive one of the digital detectors 22. The radiation source 12 and one of the digital detectors 22 may be positioned opposite one another such that radiation emitted from the radiation source 12 impinges a given digital detector 22. As noted above, the patient 18 may be positioned between the radiation source 12 and the given detector 22, such as by placing the patient 18 on the table 38 or adjacent the wall stand 40, to enable imaging of a patient anatomy. The digital detectors 22 and the overhead tube support 36 (or some other component having the radiation source 12) may be configured to communicate their position within the imaging system 34 to one or more other components of the system, such as to the system controller 28 discussed above. In addition to acquiring images from detectors placed within the receiving structures 48 and 50, the imaging system 34 may also employ one or more digital detectors in a digital cassette mode, in which the digital detectors are positioned outside of the receiving structures 48 and 50 to acquire image data.

Figure 3:
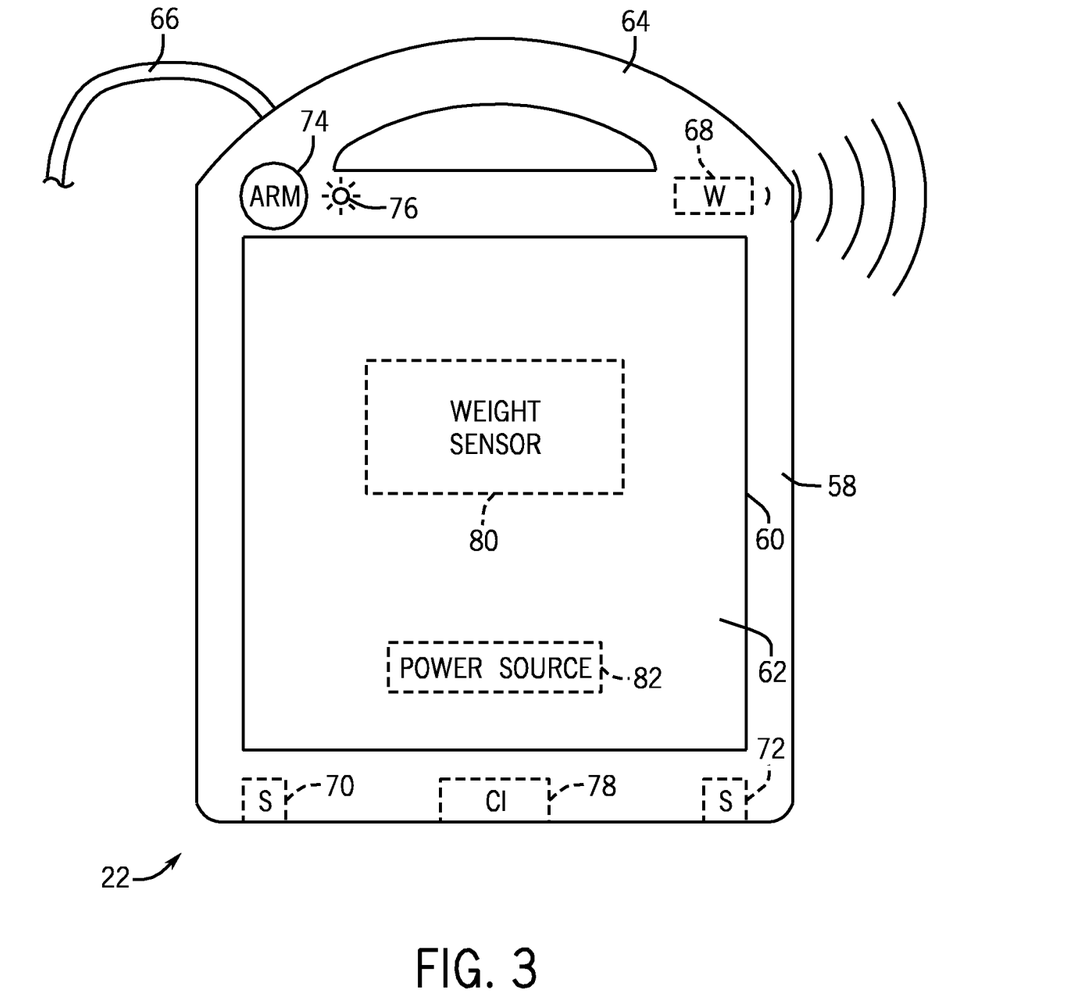
FIG. 3 is an elevational view of one embodiment of a digital detector that may be employed in the imaging system of FIGS. 2 and 3.

One example of a digital detector 22 is illustrated in FIG. 3 in accordance with one embodiment. The detector 22 may include a housing 58 that encloses various components of the detector 22. The housing 58 may include a window 60 that exposes a solid-state detector array 62 configured to receive electromagnetic radiation, such as from the radiation source 12, and convert the radiation into electrical signals that may be interpreted by the system 34 to output an image of an object or patient 18. The housing 58 may also include a handle 64 that facilitates positioning and transport of the detector 22 by a technician or other user.

As noted above, the digital detector 22 may communicate with one or more other components of an imaging system, such as the system controller 28, through a physical interface such as fixed or detachable tether 66. In some embodiments, the digital detector 22 may also (or instead) include a wireless transceiver 68 that enables the detector 22 to communicate with other components of the imaging system 34 through any suitable wireless communication protocol, such as any 802.11 communication standard. In some embodiments, the digital detector 22 may also include a communications interface 78 configured to physically engage mating interfaces 88 or 92 (FIGS. 4 and 5) of the receiving structures 48 and 50 to enable communication between the detector 22 and other components of an imaging system through such interfaces. Indeed, in one embodiment, the detector 22 may send and receive communications through the mated interfaces 78 and either 88 or 92 when disposed in one of the receiving structures 48 and 50, respectively, and through the wireless transceiver 68 when removed from the receiving structures 48 and 50.

The detector 22 may, in some embodiments, receive operating power from an external power source through the tether 66 or through the interface 78. In other embodiments, the detector 22 may include its own power source 82, such as one or more batteries, to facilitate operation of the detector 22 without inhibiting its range of movement. Additionally, the power source 82 may be recharged by an external power source through the tether 66 or the interface 78.

Figure 4:
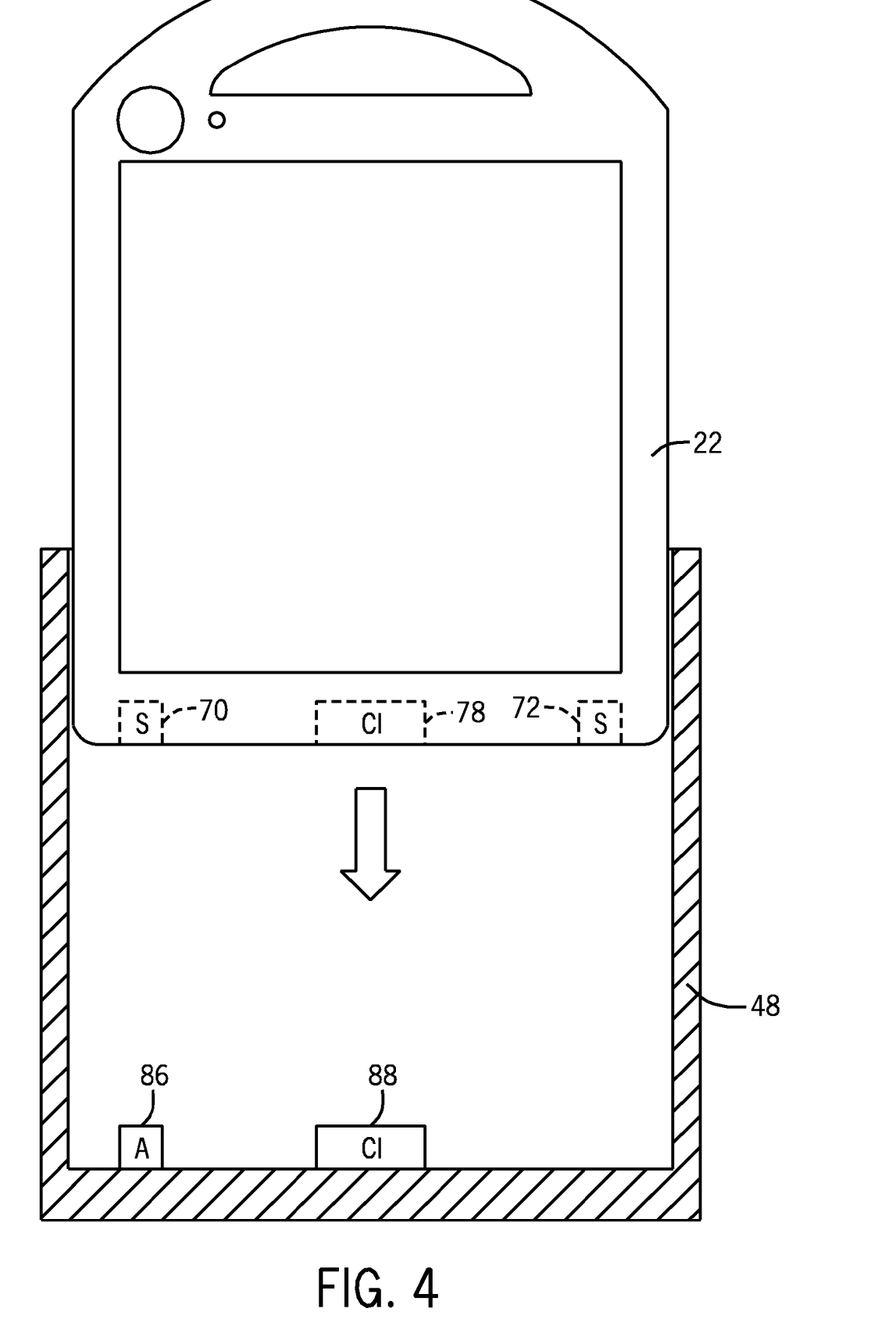
FIG. 4 generally illustrates the positioning of the digital detector of FIG. 3 into a first receiving structure of the imaging system to activate a first sensor of the detector in accordance with one embodiment.
Figure 5:
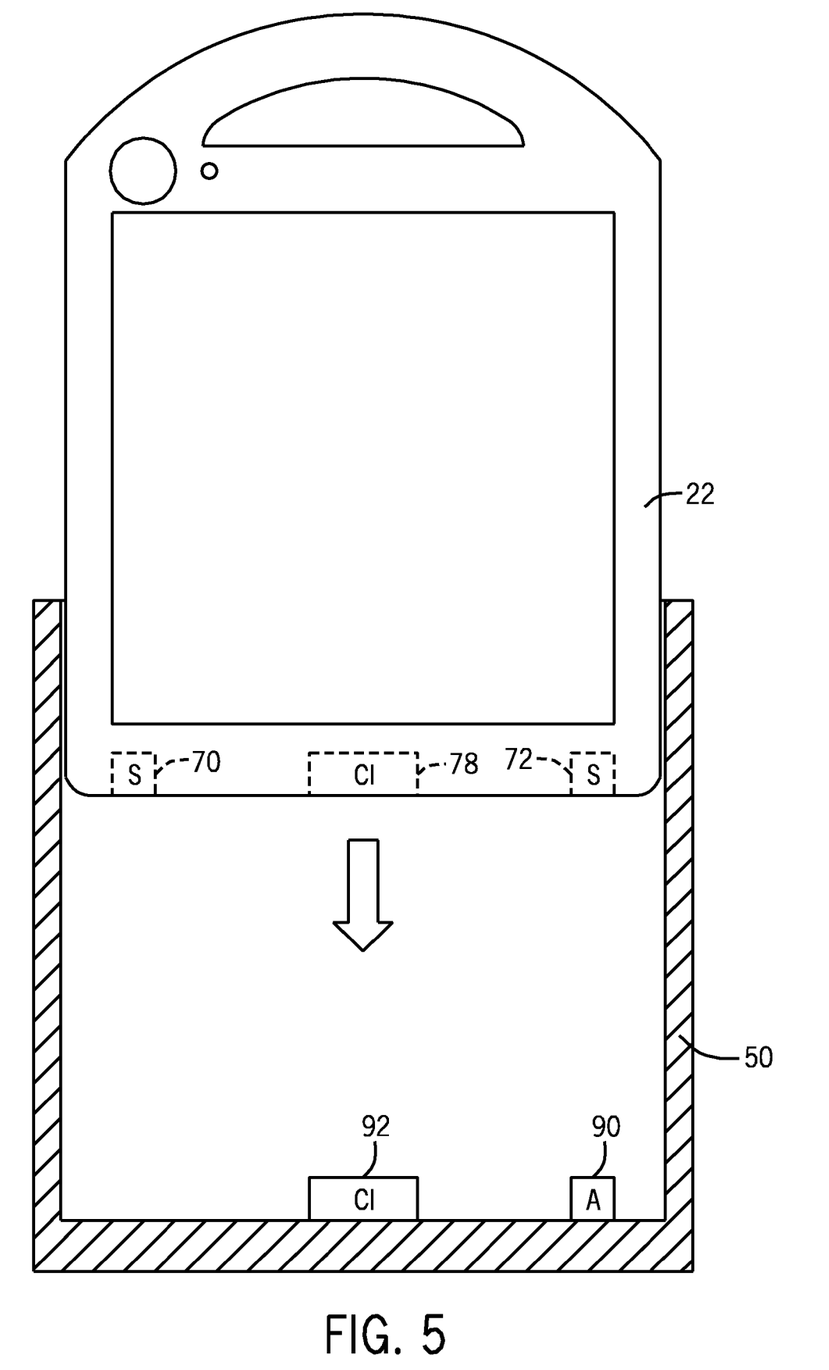
FIG. 5 generally depicts the positioning of the digital detector of FIG. 3 into a second receiving structure of the imaging system to activate a second sensor of the detector in accordance with one embodiment.

In some embodiments, the digital detector 22 may include various sensors and mechanisms configured to enable the system 34 to determine the location of the detector 22. For example, in the presently illustrated embodiment, the detector 22 may include multiple sensors, such as sensors 70 and 72, for detecting placement of the digital detector 22 at a particular location of the imaging system 34. More particularly, in accordance with one embodiment generally depicted in FIGS. 4 and 5, the sensors 70 and 72 of the digital detector 22 may be positioned on or within the housing 58 such that the sensor 70 is activated upon placement of the digital detector 22 within the receiving structure 48 of the table 38 (FIG. 4), and the sensor 72 is activated upon placement of the detector 22 within the receiving structure 50 of the wall stand 40 (FIG. 5). The receiving structure 48 may include a sensor actuator 86 disposed within the receiving structure 48 to activate the sensor 70 of the digital detector 22 upon receipt of the detector 22 by the receiving structure 48. Similarly, the receiving structure 50 may include an actuator 90 configured to activate the sensor 72 upon receipt of the digital detector 22 within the receiving structure 50.

The sensors 70 and 72, and the actuators 86 and 90, may include any of various known complimentary sensors and actuators. For instance, in some embodiments, the sensors 70 and 72 may be mechanical sensors physically activated by engagement with the actuators 86 and 90, or may include induction sensors triggered by proximity to the corresponding actuators 86 and 90. By way of further example, in another embodiment, actuators 86 and 90 may complete an electrical circuit coupled to sensors 70 and 72. In the present embodiment, the digital detector 22 may communicate its position as being within the receiving structure 48 when the sensor 70 is activated, and may report its position as being within the receiving structure 50 when the sensor 72 is activated. Additionally, the detector 22 may report that it is not in either of the receiving structures 48 and 50 when neither of the sensors 70 and 72 is activated. By determining the location of one or more detectors within the system 34, the system controller 28 may determine whether any detector 22 is positioned in an appropriate location to capture desired image data, may determine which particular detector 22 of a plurality of such detectors will receive the radiation from source 12, and may facilitate the exposure of and image acquisition from the particular detector 22.

In some embodiments, the sensors 70 and 72 could be provided in the receiving structures 48 and 50, respectively, and the actuators 86 and 90 could be provided at complimentary locations of the digital detector 22. In one such embodiment, the table 38 and the wall stand 40 may be configured to detect the presence of a digital detector 22, but they may not be configured to determine which digital detector 22 (of a group of such detectors 22) is present. In another such embodiment, however, the table 38 or wall stand 40 may communicate the activation of its sensor 70 and 72 to the received detector 22 (e.g., via communication interfaces 78 and one of 88 or 92), which may in turn communicate its position to the system controller 28. In still another such embodiment, the received detector 22 may identify itself to the table 38 or wall stand 40 once received in a respective structure 48 or 50 (e.g., via communication interfaces 78 and one of 88 or 92, respectively), and the table 38 or wall stand 40 may, in turn, be configured to communicate the presence of the identified digital detector 22 to the system controller 28. Additional embodiments are also envisaged in which the sensors 70 and 72, and the actuators 86 and 90, may be omitted from the system 34, such as certain embodiments in which communication with a detector 22 is conducted via the interface 78 and one of the interfaces 88 or 92, and in which the position of the detector can be determined with reference to the location of the interface 88 or 92 to which it is coupled.

As generally depicted in FIG. 3, in some embodiments the digital detector 22 may include an arming mechanism 74, such as a button or a switch, that may be engaged by a technician or other user to enter a digital cassette mode, in which the detector 22 may be freely moved and positioned in the system 34 independent of any particular support structure, such as receiving structures 48 and 50. Such an operational mode may facilitate cross-table imaging, such as horizontal imaging through a patient 18 on the table 38, and may facilitate imaging of the extremities of a patient 18, for example. An indicator 76, such as an LED light, an LCD display, or the like, may provide a visual indication (e.g., flashing light) to a user that the arming mechanism 74 has been engaged and that the detector 22 is operating in a digital cassette mode. Additionally, in some embodiments the digital detector 22 may include a weight sensor 80 configured to detect weight placed on the digital detector 22 and to subsequently arm the detector 22 for use in the digital cassette mode. The digital detector 22 may communicate activation of the digital cassette mode to the system controller 28, such as via the tether 66 or the wireless transceiver 68, thereby indicating to the system controller 28 which detector 22 should be managed for accurately acquiring image data.

Figure 6:
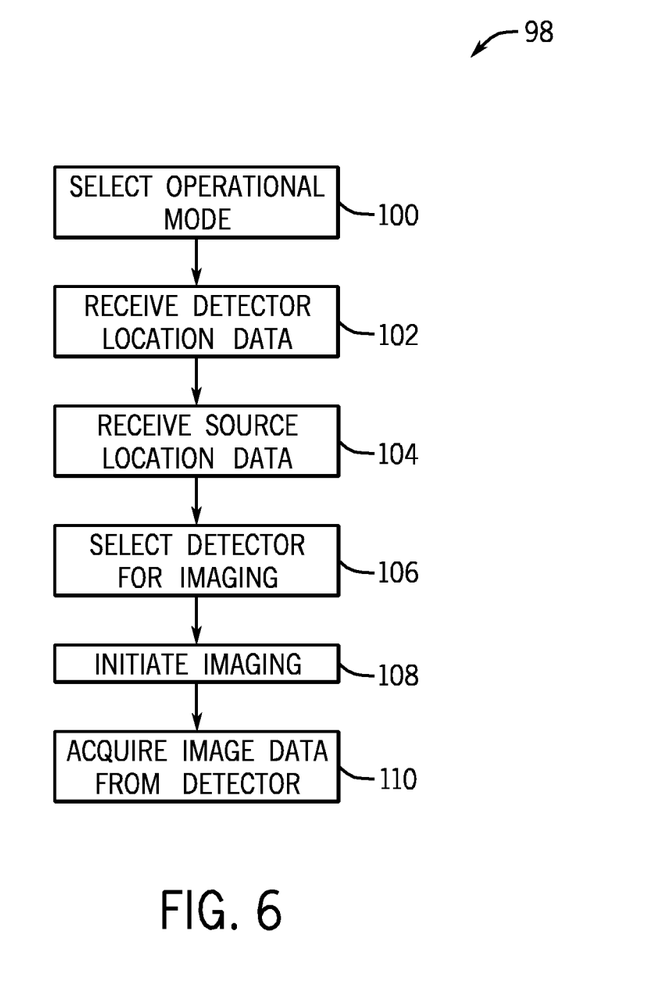
FIG. 6 is a flowchart of an exemplary method of acquiring image data from the digital detector of FIG. 3.

In one embodiment, the imaging system 34 may acquire image data through the method 98 generally depicted in FIG. 6 in accordance with one embodiment. The method 98 may include a step 100 of selecting an operational mode, such as a table mode (in which image data is to be acquired from a detector 22 received in the table 38, such as by the structure 48), a wall stand mode (in which the detector 22 is received in the wall stand 40, such as by the structure 50), or a digital cassette mode (in which the detector 22 is disposed in some other location separate from either of the receiving structures 48 and 50). The selection of the operational mode may be made by the imaging system 34, such as by the system controller 28, and in some embodiments the selection may be based on a user input. The method 98 may also include a step 102 of receiving location data from the detector 22. Such data may be sent in response to a query from the system controller 28, or may be pushed to the controller 28 by the detector 22 in real-time or at pre-determined time intervals. As used herein, "location data" refers to any communication that may be processed, such as by the system controller 28, to determine the position of a component of the imaging system. As discussed above, the detector 22 may communicate its presence within one of the receiving structures 48 and 50 or its presence at a location separate from such receiving structures. In one embodiment, the communication from the digital detector 22 may include an indication that one of the sensors 70 or 72 has been activated, and some other component of the imaging system may determine the location of the detector 22 in the table 38 or the wall stand 40 based on that indication and the position of the table 38 or the wall stand 40 as it is reported to the system controller 28. In some embodiments, the method 98 may also include a step 104 of receiving location data for the radiation source 12, such as from the overhead tube support 36.

Further, the method 98 may also include a step 106 for selecting a particular detector 22 from one or more detectors of the imaging system 34 for radiation exposure and image data acquisition. For instance, as discussed in greater detail below, if the imaging system 34 is set to a table operating mode, in which the imaging system 34 will acquire image data from a detector 22 disposed within the receiving structure 48 of the table 38, the system may determine the correct digital detector 22 to use (i.e., the detector 22 placed in the receiving structure 48) based on location data communicated by the digital detectors 22. Also, the system 34 may verify whether any detector 22 is positioned in the structure 48 before initiating exposure. Once the appropriate detector is selected, the method 98 may proceed to a step 108 of initiating the imaging process, such as by exposing the selected detector 22 to a radiation beam from the radiation source 12. Based on the location of the radiation source 12 and a particular detector 22, the system controller 28 of one embodiment may verify that these components are positioned at desired locations before initiating the imaging process. The image data received by the detector 22 may then be acquired from the detector 22 in a step 110.

Figure 7:
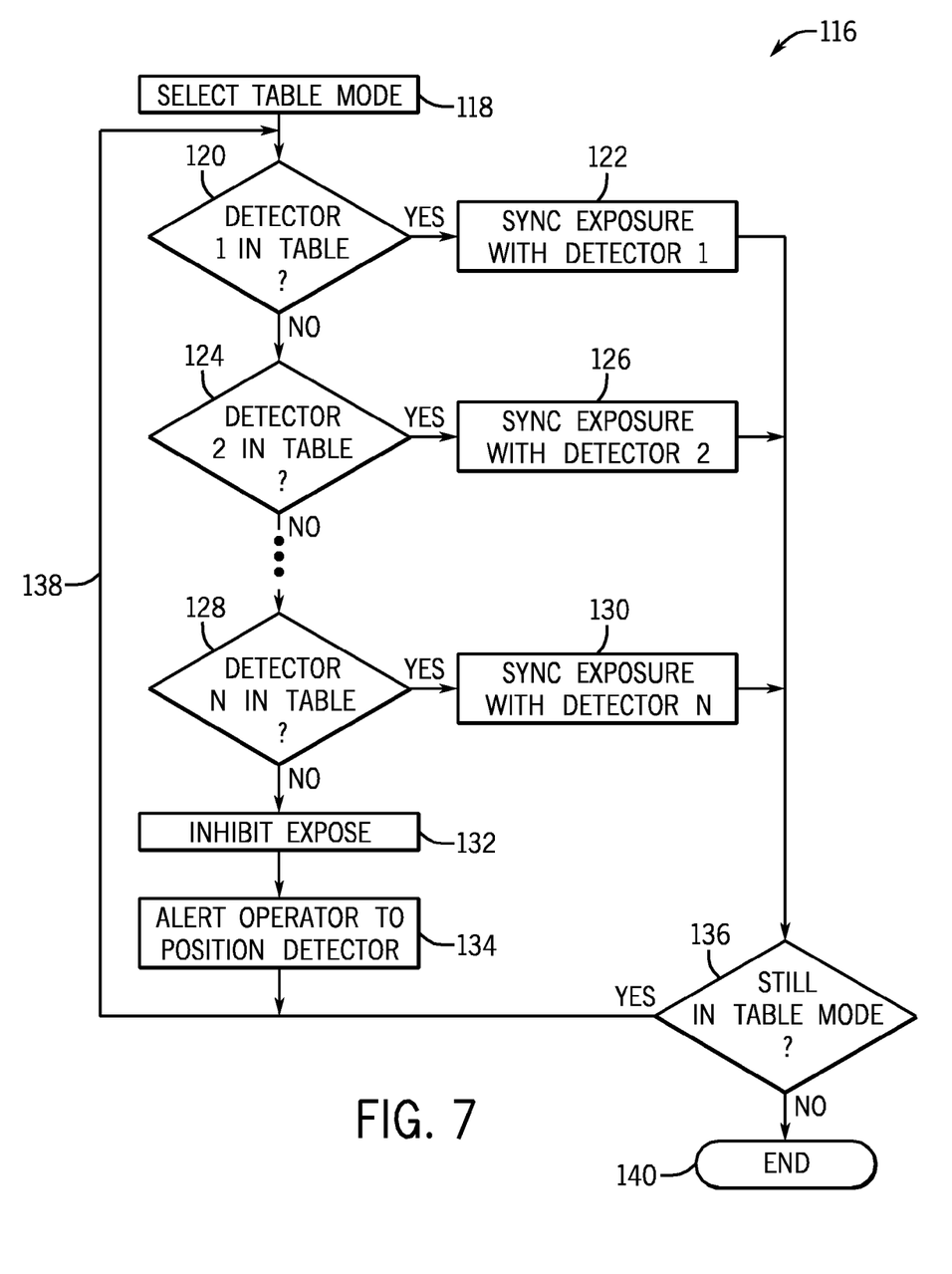
FIG. 7 is a flowchart of a method of operating an imaging system in a first operational mode to acquire image data from a digital detector at a first location of the imaging system in accordance with one embodiment.
Figure 8:
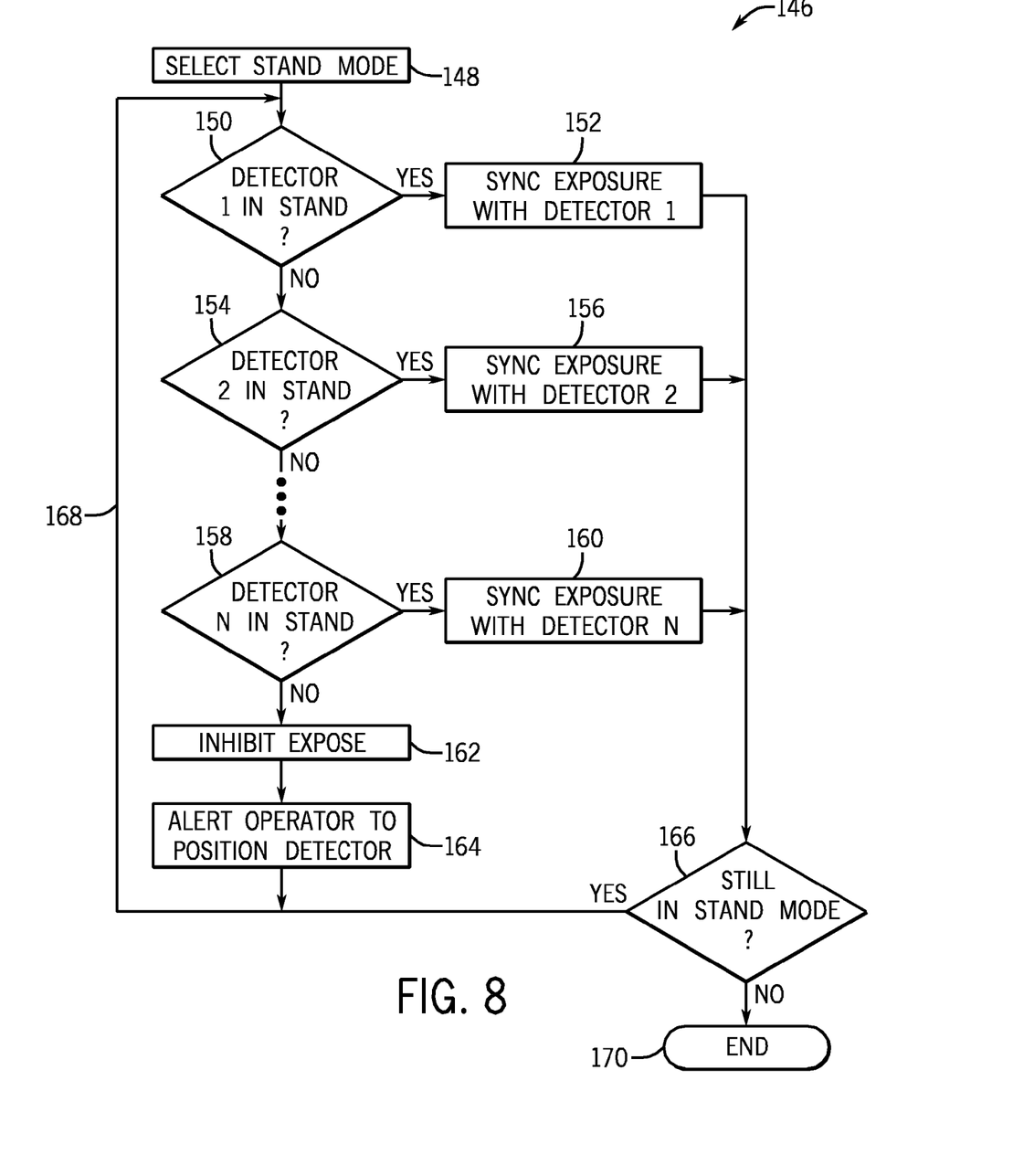
FIG. 8 is a flowchart of a method of operating an imaging system in a second operational mode to acquire image data from a digital detector at a second location of the imaging system in accordance with one embodiment.
Figure 9:
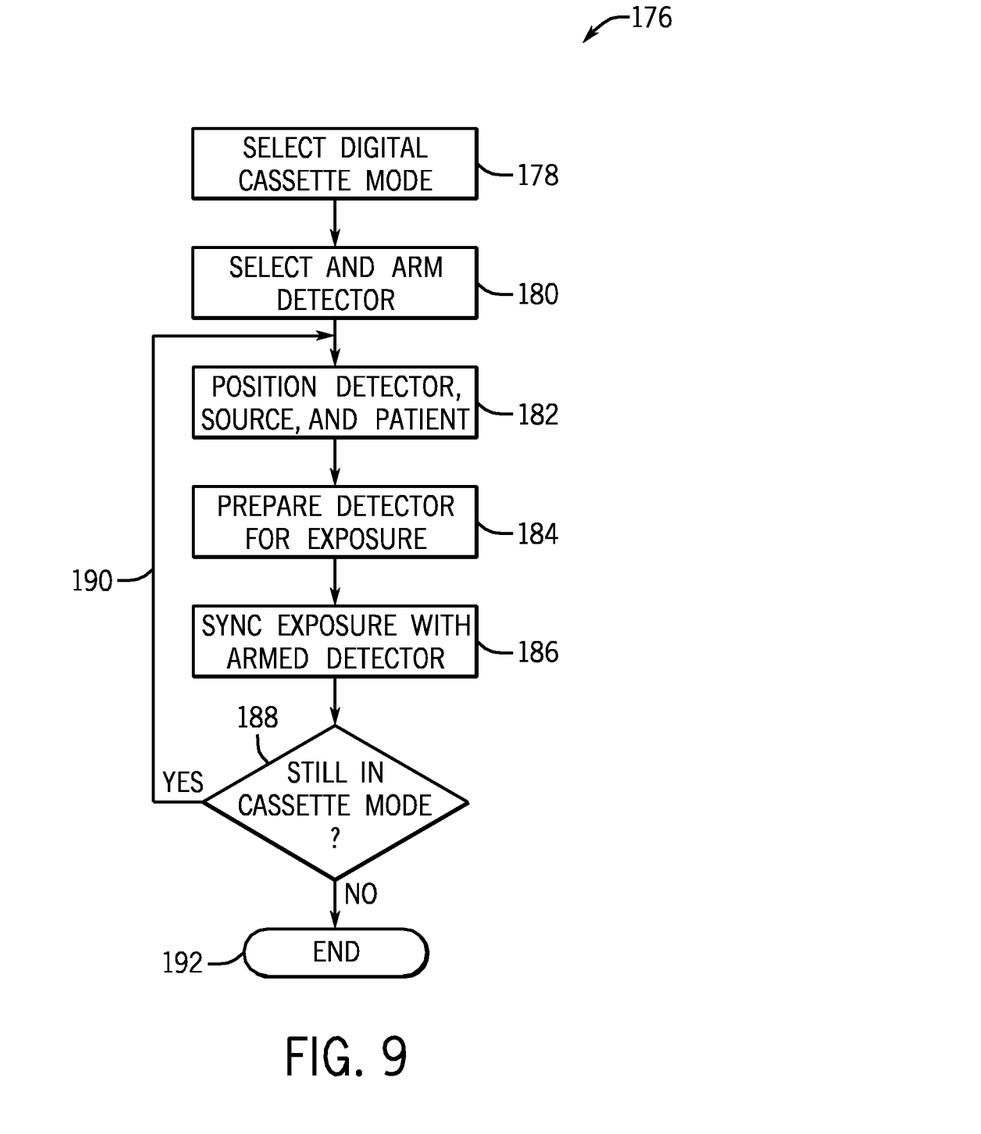
FIG. 9 is a flowchart of a method of operating an imaging system in a third operational mode to acquire image data from a digital detector in accordance with another embodiment.

Examples of workflows for various potential operating modes of the imaging system 34 are generally depicted in FIGS. 7-9 in accordance with certain embodiments. In FIG. 7, a method 116 is depicted, which may include selecting a table operating mode in a step 118. As represented by decision block 120, the method 116 may include determining whether a first detector 22 is positioned within the table 38, such as within the receiving structure 48. If this first detector 22 is, in fact, positioned in the table 38 (which may be determined based on location data communicated from the first detector 22, as generally discussed above), the system controller 28 may synchronize exposure between the source 12 and the first detector in a step 122. Otherwise, the method 116 may proceed to determine whether a second detector 22 is positioned within the table 38, as generally indicated by decision block 124. Exposure may be synchronized between the source 12 and the second detector 22 in a step 126 if the second detector is in the table 38. In some embodiments, the method 116 may also include determining whether other detectors 22 are positioned within the table, as generally indicated by decision block 128, and may proceed to synchronize exposure of any detector 22 determined to be within the table 38 in a step 130. If no detector 22 is determined to be in the table 38, the method may inhibit the exposure process in a step 132, and may alert an operator or technician to position a detector 22 within the table in a step 134. While the imaging system 34 remains in the table mode, the foregoing steps may be reiterated to acquire additional images, as generally indicated by reference numbers 136 and 138. Following such image acquisition, the imaging system 34 may be set to a different operating mode, placed in a standby mode, or powered off, and the method 116 may end, as generally indicated by reference number 140.

The imaging system 34 may also operate in another mode, such as in accordance with a method 146 of one embodiment generally depicted in FIG. 8. For example, the imaging system 34 may be operated in a stand mode to acquire data from a detector placed in the wall stand 40. The workflow of method 146 may, in at least some embodiments, be similar to that of method 116. For instance, the method 146 may include selecting a table operating mode in a step 148. The method may also include determining which detector 22, if any, is positioned within the wall stand 40 (e.g., within the receiving structure 50, as generally indicated by decision blocks 150, 154, and 158. In some embodiments, the sensor 72 of the detector 22 positioned in the wall stand 40 will be activated by the actuator 90, as discussed above with reference to FIG. 5, thus facilitating identification of the appropriately positioned detector 22 by the system controller 28. Upon detection of a particular detector 22 within the wall stand 40, that detector 22 may be synchronized with the source 12 and exposed to acquire image data, as generally represented by steps 152, 156, and 160. As noted above with respect to operation in a table mode, the method 146 may also include steps 162 and 164 of inhibiting an exposure if no detector 22 is detected in the wall stand 40, and alerting an operator to position a detector 22 in the wall stand 40. These previous steps of method 146 may be repeated while the imaging system 34 remains in the stand mode, as generally indicated by reference numbers 166 and 168, before concluding at block 170.

The imaging system 34 may also acquire data via a method 176 in accordance with one embodiment generally depicted in FIG. 9. In a step 178 of the method 176, the imaging system 34 may select a digital cassette operating mode, which is generally described above, to facilitate use of a digital detector 22 separate from the table 38 and the wall stand 40. A technician or other user may select a desired digital detector 22 and arm the detector for exposure in a step 180. As may be appreciated from the discussion above, in some embodiments the technician may arm a particular digital detector 22 by engaging its arming mechanism 74. In other embodiments, however, a technician or the imaging system 34 may select a particular detector 22 in some other manner. For example, a detector 22 may include a weight sensor 80, and the detector 22 may be armed automatically upon sensing weight placed upon the detector 22. The armed detector 22 may stay armed until the imaging system 34 is set to some other operating mode (including standby and power off modes), or until another detector 22 is armed. In another embodiment, the system controller 28 may inhibit exposure if more than one detector is armed.

In a step 182, the selected detector 22, the source 12, and the patient 18 may be positioned such that radiation from the source 12 will pass through a desired anatomy of the patient 18 and impinge the detector 22. The method 176 may also include a step 184 of preparing the armed detector 22 for exposure, and synchronizing the exposure between the source 12 and the armed detector 22 in a step 186. The imaging system 34 may continue to acquire additional image data or may conclude, as generally indicated by reference numbers 188, 190, and 192.

Technical effects of the invention include the ability to accurately and efficiently determine that a digital detector is positioned in a desired location prior to exposure, and to select a correctly positioned detector from a plurality of detectors. In at least some embodiments, the presently disclosed techniques reduce the incidence of exposing an incorrect detector in a multi-detector system and of exposing a patient to radiation prior to placement of a detector in a position to receive the radiation. Consequently, technical effects of the invention also include a reduction in the likelihood of operator errors during imaging processes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system comprising:
   a radiation source;
   a digital detector;
   a first receiving structure and a second receiving structure each configured to receive the digital detector; and
   system control circuitry configured to control exposure of the digital detector by the radiation source and to acquire image data from the digital detector;
   at least two location sensors and at least two sensor actuators configured to activate the at least two location sensors, wherein the digital detector includes the at least two location sensors and the first receiving structure and the second receiving structure each include a respective sensor actuator of the at least two sensor actuators to activate different location sensors of the at least two location sensors of the digital detector, or wherein the digital detector includes the at least two sensor actuators and the first receiving structure and the second receiving structure each include a respective location sensor of the at least two location sensors to be activated by a different one of the at least two sensor actuators of the digital detector;
   wherein the digital detector is configured to communicate its location to the system control circuitry based on receipt of the digital detector by the first or second receiving structures.

2. The imaging system of claim 1, comprising a patient table including the first receiving structure, such that the digital detector communicates its location at the patient table based on receipt of the digital detector in the first receiving structure.

3. The imaging system of claim 1, comprising a wall stand including the second receiving structure, such that the digital detector communicates its location at the wall stand based on receipt of the digital detector in the second receiving structure.

4. The imaging system of claim 1, wherein the digital detector includes first and second location sensors, and the first and second receiving structures include respective first and second sensor actuators, wherein the first sensor actuator of the first receiving structure is configured to activate the first location sensor upon receipt of the digital detector by the first receiving structure, and the second sensor actuator of the second receiving structure is configured to activate the second location sensor upon receipt of the digital detector by the second receiving structure.

5. The imaging system of claim 1, wherein the imaging system is configured to facilitate operation of the digital detector in a digital cassette mode apart from the first and second receiving structures.

6. The imaging system of claim 5, wherein the digital detector is configured to allow a user to activate the digital cassette mode through user-interaction with a mechanism disposed on the digital detector.

7. The imaging system of claim 5, wherein the digital detector includes a weight sensor configured to detect when an object has been placed on the digital detector, and wherein the digital detector is configured to automatically facilitate the digital cassette mode when the weight sensor detects that the object has been placed on the digital detector.

8. The imaging system of claim 1, wherein the radiation source includes an X-ray radiation source.

9. A digital X-ray detector comprising:
   a first sensor configured to be actuated by a first actuator that is positioned at a first location of an X-ray imaging system;
   a second sensor disposed at a different location of the digital X-ray detector than the first sensor and configured to be actuated by a second actuator that is positioned at a second location of the X-ray imaging system;
   wherein the digital X-ray detector is configured to communicate to a system controller of the X-ray imaging system a signal indicative of the presence of the digital X-ray detector at the first location of the X-ray imaging system upon actuation of the first sensor by the first actuator, and a signal indicative of the presence of the digital X-ray detector at the second location of the X-ray imaging system upon actuation of the second sensor by the second actuator.

10. The digital X-ray detector of claim 9, wherein the first location is at a table of the X-ray system.

11. The digital X-ray detector of claim 9, wherein the second location is at a wall stand of the X-ray system.

12. The digital X-ray detector of claim 9, comprising an external mechanism configured to be engaged by a user of the digital X-ray detector to arm the digital X-ray detector for use at additional locations other than the first and second locations, wherein the digital X-ray detector is configured to communicate to the system controller, upon engagement of the external mechanism, a signal indicating that the digital X-ray detector is not positioned at either of the first and second locations.

13. The digital X-ray detector of claim 12, wherein the external mechanism includes at least one of a button or a switch.

14. The digital X-ray detector of claim 12, comprising a visual indicator configured to output at least an indication of whether the digital X-ray detector has been armed for use at the additional locations other than the first and second locations.

15. The digital X-ray detector of claim 9, wherein the digital X-ray detector is configured to wirelessly communicate with the system controller of the X-ray imaging system.

16. A method comprising:
   using a control processor of an X-ray imaging system to perform the steps of:
      receiving a user input indicative of an operational mode for the X-ray imaging system, wherein receiving the user input indicative of the operational mode includes receiving a signal indicative of a user selection between at least a table mode, a wall stand mode, and a digital cassette mode of operating the X-ray imaging system;
      receiving location data pertaining to one or more digital detectors of the X-ray imaging system;
      selecting, from the one or more digital detectors, a particular digital detector to be exposed for an image acquisition procedure of the X-ray imaging system based on the location data and the user selection between at least the table mode, the wall stand mode, and the digital cassette mode;
      initiating the image acquisition procedure to expose the particular digital detector with X-rays from a radiation source of the X-ray imaging system; and
      acquiring image data from the particular digital detector, the image data representative of an object located between the radiation source and the particular digital detector during the image acquisition procedure.

17. The method of claim 16, wherein receiving location data pertaining to the one or more digital detectors includes:
   querying at least one digital detector of the one or more digital detectors for the location data; and receiving the location data from the at least one digital detector in response to the querying.

18. The method of claim 16, comprising using the control processor to receive location data pertaining to the radiation source, wherein initiating the image acquisition procedure to expose the particular digital detector with X-rays from a radiation source of the X-ray imaging system is performed after a determination by the control processor, based on the location data pertaining to the radiation source and the location data pertaining to the particular digital detector, that the radiation source and the particular detector are disposed in desired locations.

* * * * *